United States Patent [19]
Hiller et al.

[11] 3,962,300
[45] June 8, 1976

[54] PROCESS FOR PRODUCING METHANOL

[75] Inventors: Heinz Hiller, Bad Vilbel; Gerhard Hochgesand, Neu Isenburg; Emil Supp, Frankfurt am Main; Friedemann Marschner, Weisskirchen; Gerhard Grunewald, Mainz-Mombach, all of Germany

[73] Assignee: Metallgesellschaft Aktiengesellschaft, Frankfurt am Main, Germany

[22] Filed: Apr. 15, 1975

[21] Appl. No.: 568,532

Related U.S. Application Data

[63] Continuation-in-part of Ser. No. 350,849, April 13, 1973, abandoned, which is a continuation-in-part of Ser. No. 130,693, April 2, 1971, abandoned.

[30] Foreign Application Priority Data
May 19, 1970  Germany............................ 2024301

[52] U.S. Cl............................. 260/449.5; 252/373
[51] Int. Cl.²....................................... C07C 29/16
[58] Field of Search.................. 260/449.5; 252/373

[56] References Cited
UNITED STATES PATENTS

| | | | |
|---|---|---|---|
| 2,964,551 | 12/1960 | Woolcock........................ | 260/449.5 |
| 2,999,741 | 9/1961 | Dille et al........................ | 252/373 |
| 3,064,029 | 11/1962 | White............................... | 260/449.5 |
| 3,071,453 | 1/1963 | James........................... | 260/449.5 X |
| 3,441,393 | 4/1969 | Finneran et al................. | 252/373 |
| 3,501,516 | 3/1970 | Parrish............................ | 260/449.5 |
| 3,532,467 | 10/1970 | Smith et al....................... | 252/373 |
| 3,597,465 | 8/1971 | Karafian et al................. | 260/449.5 |

FOREIGN PATENTS OR APPLICATIONS

| | | | |
|---|---|---|---|
| 2,024,301 | 12/1971 | Germany....................... | 260/449.5 |
| 6,812,176 | 3/1969 | Netherlands.................... | 260/449.5 |
| 1,164,407 | 9/1918 | United Kingdom.............. | 252/373 |
| 1,169,241 | 10/1969 | United Kingdom.............. | 260/449.5 |

*Primary Examiner*—Howard T. Mars
*Attorney, Agent, or Firm*—Burgess, Dinklage & Sprung

[57] ABSTRACT

Methanol is produced by a process wherein
1. sulfur-containing high-boiling hydrocarbons are subjected to a partial oxidizing treatment with oxygen and water vapor at a pressure which is at least 5 kilograms and preferably 10-15 kilograms per square centimeter above the pressure of the methanol synthesis to produce a raw gas;
2. the raw gas is desulfurized and is subsequently treated with water vapor to convert part of its carbon monoxide content into hydrogen and carbon dioxide;
3. thereafter the converted gas from step (2) is scrubbed to remove at least part of the carbon dioxide;
4. methanol is produced by a reaction of the resulting synthesis gas from step (3) in contact with a copper-containing catalyst, which is indirectly cooled with water boiling under superatmospheric pressure resulting in the production of high-pressure steam; and
5. the high-pressure steam produced by the exothermic heat of formation of the methanol in step (4) is expanded by generating power to produce compression energy for the gases to be compressed in the process.

9 Claims, 1 Drawing Figure

U.S. Patent June 8, 1976 3,962,300
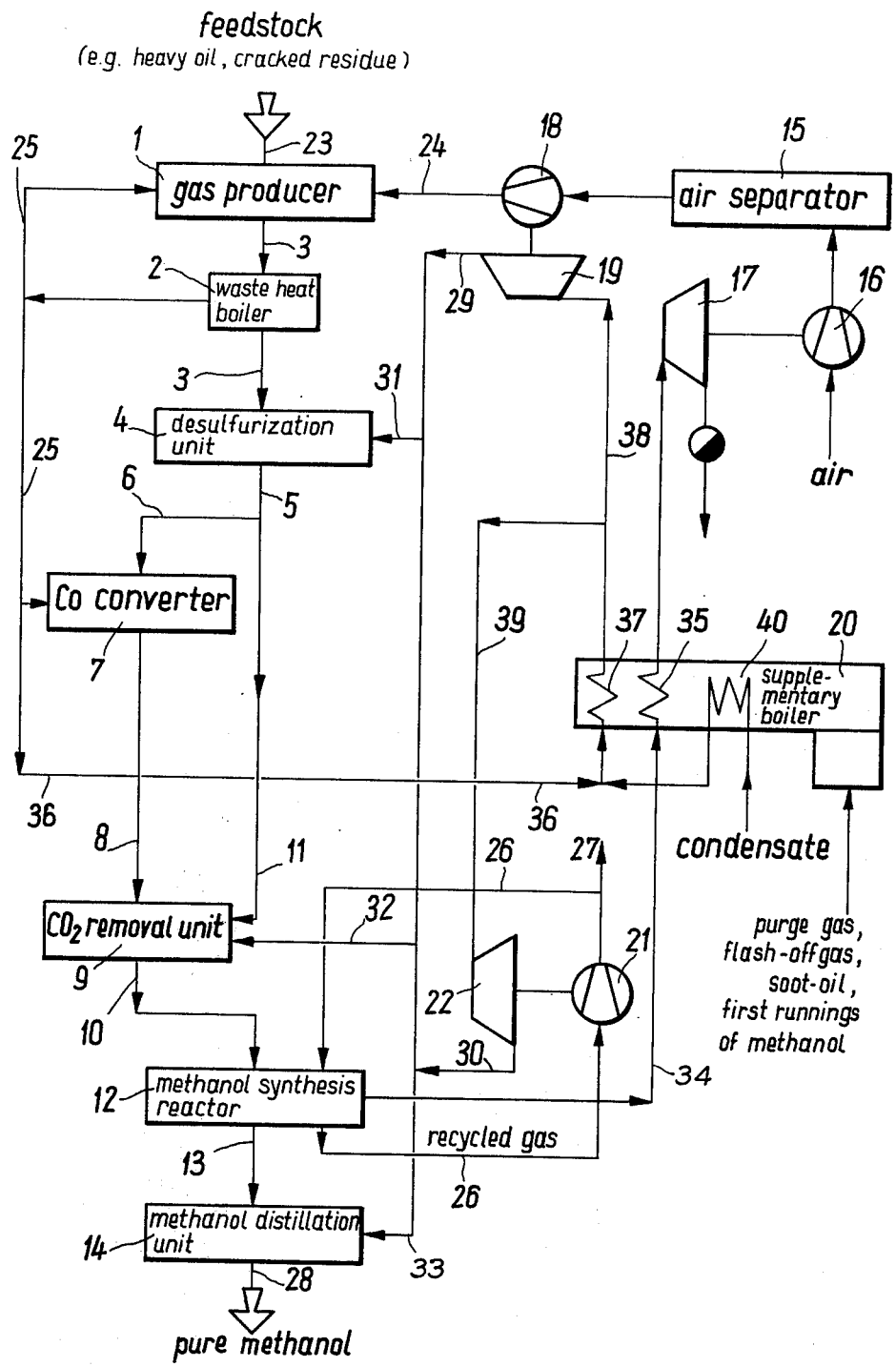

PROCESS FOR PRODUCING METHANOL

RELATED APPLICATIONS

This application is a continuation-in-part of application Ser. No. 350,849 filed Apr. 13, 1973 now abandoned, which is in turn a continuation-in-part of application Ser. No. 130,693 filed Apr. 2, 1971 now abandoned.

BACKGROUND

The production of methanol from carbon monoxide and hydrogen in contact with catalysts is a highly exothermic reaction, which involves a volumetric contraction.

The commercial synthesis of methanol has been carried out for a long time in high-pressure reactors under pressures of 100–300 kilograms per square centimeter and at temperatures of about 320°–380°C. in contact with catalysts which contain oxides of zinc and chromium. To enable a dissipation of the heat of reaction, the catalyst in the high-pressure reactor is divided into layers and cold fresh synthesis gas is added to the reaction mixture between these layers. It is also known to provide heat exchange elements, which are disposed in or between the catalyst layers through which flows a cooling fluid. The utilization of the surplus heat of reaction by means of such heat exchange elements involves a high structural expenditure and also involves considerable difficulties owing to the high temperature level.

Copper-containing catalysts having a higher activity have recently been developed. Methanol can be synthesized in contact with these catalysts under pressures less than 100 kilograms per square centimeter (absolute pressure) and at temperatures of 230°–270°C. Medium-pressure equipment may be used for reaction under such conditions.

This means, for example, that piston compressors may be replaced by rotating compressors and considerable savings of material are enabled in the overall plant.

In a special embodiment of that process, the catalyst is disposed in the tubes of a tubular reactor, which is indirectly cooled by water boiling under super-atmospheric pressure. In this way the heat of reaction to be dissipated is utilized as high-grade energy in the form of high-pressure steam.

Synthesis gases for the production of methanol consist of $H_2$ and CO and may contain $CO_2$. They must be free of sulfur and should contain as little inert gas as possible. Inert gases in the reaction to produce methanol are nitrogen, argon and methane. Suitable synthesis gases may be produced in a tube furnace by a cracking of gaseous hydrocarbons or of liquid evaporable hydrocarbons having a final boiling point of about 200°C. by a treatment with water vapor in contact with indirectly heated catalysts which contain nickel and under pressures of 5–30 kilograms per square centimeter and at temperatures of 750°–900°C. Because the feedstocks, preferably natural gas or light gasoline, are in most cases available in a sulfur-free condition, the cracked gas obtained as a primary product can be compressed to the synthesis pressure when the water vapor has been removed from the gas by condensation whereas a special purification is not required. The compressed cracked gas can be introduced into the reactor.

The synthesis of methanol is a large-scale chemical process in which low-cost feedstocks are preferred. For this reason a considerable part of the synthesis gases containing CO and $H_2$ is produced by partial oxidation, suitably in the presence of steam, from heavy hydrocarbon oils, such as heavy fuel oils or residual oils obtained by the distillation or cracking of petroleum. Pure oxygen is required in these processes if the synthesis gas has to be free of inert gases. Besides, the cracked gas obtained as a primary product contains sulfur. It has been found that the synthesis of methanol carried out under a pressure of 30–60 kilograms per square centimeter above atmospheric pressure and at a temperature of 240°–270°C. can be combined in a highly desirable manner with the production of synthesis gas by a partial oxidation treatment of heavy hydrocarbon oils with pure oxygen in the presence of water vapor, and with the required purification of the gas, if the synthesis itself is carried out in a catalyst which is indirectly cooled by water boiling under superatmospheric pressure and the raw synthesis gas is produced under a pressure which is at least 5 and preferably 10–15 kilograms per square centimeter higher than the pressure of the methanol synthesis. In this process, the need for a compression of the synthesis gas before the synthesis reactor is eliminated and the high-pressure steam produced in said reactor is available to supply the compression energy which is consumed in the process. By expanding this steam to atmospheric pressure, about 270 kWh per metric ton of methanol product can be generated. This is more than one-half of the compression energy required in the overall process and about 70% of the compression energy required for the production of the compressed pure oxygen by a low-temperature separation of air.

Additional high-pressure steam is available from the waste heat boiler associated with the gas producer and may be used for the gasifying reaction and for the conversion of the carbon monoxide in a partial stream of the raw gas to carbon dioxide and hydrogen. The remaining surplus of said high-pressure steam may be used for the production of power. Any residual amount of steam which is required may be produced in a supplementary boiler, which is fired with the by-products of the methanol synthesis, such as dimethyl ether, the residual synthesis gas (purge gas), the first runnings obtained by the distillation of methanol, and the soot-oil obtained by the purification of the raw synthesis gas. The supplementary boiler serves also to superheat the steam required for a production of power.

SUMMARY

The invention relates to a process of producing methanol by a reaction of a synthesis gas which contains oxides of carbon and of hydrogen at 230°–280°C. and under a pressure of 30–80 kilograms per square centimeter (absolute pressure) in contact with a copper-containing catalyst.

The process according to the invention is characterized in that 1. sulfur-containing high-boiling hydrocarbons are subjected to a partial oxidizing treatment with oxygen and water vapor at a pressure which is at least 5 kilograms and preferably 10–15 kilograms per square centimeter above the pressure of the methanol synthesis to produce a raw gas;

2. the raw gas is desulfurized and is subsequently treated with water vapor to convert part of its carbon monoxide content into hydrogen and carbon dioxide;

3. thereafter the converted gas from step (2) is scrubbed to remove at least part of the carbon dioxide;

4. methanol is produced by a reaction of the resulting synthesis gas from step (3) in contact with a copper-containing catalyst, which is indirectly cooled with water boiling under superatmospheric pressure resulting in the production of high-pressure steam; and 5. the high-pressure steam produced by the exothermic heat of formation of the methanol in step (4) is expanded by generating power to produce compression energy for the gases to be compressed in the process.

DESCRIPTION

The high-pressure steam produced by the heat of formation of methanol may be expanded to ambient pressure with recovery of the compression energy required to compress the air from which the pure oxygen is recovered. The compression energy required to compress the pure oxygen and the recycled synthesis gas which is recirculated through the methanol synthesis reactor and the methanol separator is supplied by part of the high-pressure steam from the waste heat boiler associated with the gas producer. The high-pressure steam is only partly expanded in back-pressure turbines. The resulting low-pressure steam is used to heat the methanol distillation unit and the regenerating plant associated with the scrubber for removing carbon dioxide.

The pressure of the steam produced in the waste heat boiler should be higher than the pressure under which the gas is produced by a partial oxidation of heavy hydrocarbons so that this high-pressure steam can be introduced directly into the gasification reactor and into the carbon monoxide converter which is fed with the primary cracked gas when it has been desulfurized.

On the other hand, the high-pressure steam produced by the heat of formation of methanol may be partly expanded in the driving turbines for the oxygen compressor and for recirculating the recycled gas and may then be used to heat the methanol distillation unit and the regenerating plant associated with the scrubber for removing the carbon dioxide. In that case, the compression energy required to compress the air is supplied by the high-pressure steam produced in the waste heat boiler associated with the gas producer.

The scrubbing of the primary cracked gas to remove all sulfur compounds and the scrubbing of that partial stream of the desulfurized raw gas which is passed through the carbon monoxide converter to remove carbon dioxide are usually carried out in known manner with methanol at temperatures below 0°C. In the first place, the absorbent is available as an end product of the process. Moreover, absorbent which is carried by the pure gas out of the scrubbing tower need not be recovered. Finally, that step of the regenerating process in which the recirculated methanol used as an absorbent is separated from the absorbed water may be combined with the distillation of the raw methanol product.

Because the copper-containing catalyst for the methanol synthesis is highly susceptible to sulfur, that partial stream of the desulfurized cracked gas which has not been passed through the carbon monoxide converter may also be passed through an additional scrubbing stage fed with methanol so that an ingress of sulfur compound into the synthesis reactor will be reliably avoided even when the desulfurization is not performed satisfactorily. This additional scrubbing stage may constitute a fine scrubbing stage consisting of a few plates disposed in the upper section of the scrubbing column for the removal of $CO_2$ and is fed with fully regenerated absorbent whereas the lower section, in which a major portion of the $CO_2$ is removed fro the converted gas, is fed with absorbent which has partly been regenerated by being expanded to atmospheric or a subatmospheric pressure and, if desired, by being stripped with an inert gas, e.g., with the nitrogen which is available from the oxygen recovery plant. In an intermediate section, the column is fed with partly regenerated absorbent, which mixes with the absorbent flowing down from the fine scrubbing zone. The intermediate section of the column is also fed with that partial stream which has been desulfurized only and now mixes with the converted gas stream having a low $CO_2$ content. The number of plates and the rate of absorbent in the fine scrubbing zone are selected so that the out-flowing pure gas has the desired content of residual $CO_2$ whereas any traces of sulfur compounds which have passed through the desulfurizing unit will be reliably retained.

DESCRIPTION OF THE DRAWING

The accompanying drawing is a flow scheme for carrying out the process of the present invention for producing methanol.

The drawing shows by way of example the flow scheme of a plant for carrying out the process according to the invention. The plant consists substantially of a gas producer 1, a waste heat boiler 2 associated therewith, a gas-desulfurizing unit 4, a carbon monoxide converter 7, which is succeeded by a scrubber 9, for removing $CO_2$, a synthesis reactor 12, a methanol distillation unit 14, an air separator 15 and a supplementary boiler 20 for superheating and producing steam. The plant comprises compressors 16, 18, 21, which are driven by steam turbines 17, 19, 22.

The gas producer 1 has associated with it a unit, not shown, which succeeds the waste heat boiler 2 and serves to remove soot from the raw cracked gas. As much as possible of the soot which is removed here is admixed to the heavy oil used as a feedstock. The surplus to be discarded is burnt under a supplementary boiler 20.

The gas desulfurization unit 4 and the scrubber for the removal of $CO_2$ are absorption units, in which methanol is used as an absorbent at temperature below 0°C.

The laden absorbents from both process steps may be regenerated separately or in a common desorption stage. The conversion of carbon monoxide in unit 7 is carried out in known manner in contact with an iron oxide-chromium-oxide catalyst.

The feedstock, e.g., the sulfur-containing residual oils produced by the distillation of a cracked oil, is supplied through conduit 23 to the gas producer 1, in which it is reacted with pure oxygen supplied through conduit 24 and with water vapor supplied through conduit 25. The reaction is carried out at a temperature of about 1400°C. and under a pressure of about 55 kilograms per square centimeter. The raw cracked gas flows in conduit 3 and through the waste heat boiler 2 to the gas desulfurization unit 4. The desulfurized gas is divided into two partial streams flowing in conduits 4 and 6, respectively. Conduit 6 leads to the carbon monoxide converter 7, to which is fed supplementary water vapor from conduit 25. The partial stream which has become enriched with hydrogen in the carbon monoxide converter is conducted in conduit 8 to the scrubber 9 for the removal of $CO_2$ and in or behind that scrubber is admixed to the desulfurized partial stream from conduit 11 to form the peculiar synthesis gas, which flows in conduit 10 into the synthesis reactor 12. The synthesis reactor 12 is provided with a separator, not shown, and with a ring conduit 26, in which the recycled synthesis gas is recirculated through the reactor and separator by means of the compressor. A stream of residual synthesis gas (purge gas) is discharged through conduit 27 and burnt in the supplementary boiler 20.

The raw methanol recovered in the separator which is associated with the methanol synthesis reactor is conducted in conduit 13 to the distillation unit 14, which discharges pure methanol through conduit 23. The methanol distillation unit is heated with low-pressure steam discharged from the back-pressure turbines 19 and 22, from which steam flows through conduits 29, 30, 31, 32, 33 to the methanol distillation unit 14 and the desorption units which are associated with the desulfurization unit 4 and the $CO_2$-removing scrubber 9.

Steam under a pressure of about 38 kilograms per square centimeter (absolute pressure) is produced in the synthesis reactor 12 and passed in conduit 34 through a superheater 35 of the supplementary boiler to the expansion turbine 17, which drives the air compressor 16 preceding the air separator 15. That part of the high-pressure steam from the waste heat boiler 2 which is not consumed in the cracking reaction carried out in the gas producer 1 and in the conversion of carbon monoxide in unit 7 is conducted in conduit 36 through a superheater 37 in the supplementary boiler 20 and is supplied through conduits 38 and 39 to the back-pressure steam turbines 19 and 22.

The supplementary boiler comprises the superheaters 35 and 37 and an evaporator, in which additional steam for driving the turbines 19 and 22 can be produced from condensate. The fuel burnt in the supplementary boiler consists of waste products formed in the process, specifically, of the residual synthesis gas from conduit 27 and the gaseous and liquid components in the first runnings from the methanol distillation unit and of the surplus soot produced in the gas-producing plant.

The following example should facilitate the full understanding of the invention.

EXAMPLE

A mixture of cracked residual oil and of soot oil produced in the soot-processing unit of the gas-producing plant is prepared and has the following composition in percent by weight:

| | |
|---|---|
| C | 82.875 |
| H | 10.748 |
| N | 0.361 |
| O | 2.177 |
| S | 3.800 |
| Ash | 0.039 |

840 kilograms of said mixture are gasified in 1 under a pressure of 55 kilograms per square centimeter above atmospheric pressure and at a temperature of about 1400°C. by a partial oxidation treatment with 612 standard cubic meters oxygen (99.5% pure) and 378 kilograms water vapor. 2370 standard cubic meters raw gas are thus produced, which has the following composition in percent by volume:

| | |
|---|---|
| $CO_2$ | 5.26 |
| CO | 47.09 |
| $H_2$ | 46.03 |
| $CH_4$ | 0.45 |
| $N_2$ + Ar | 0.23 |
| $H_2S$ + COS | 0.94 |

In the waste heat boiler 2, the waste heat of the cracked gas is utilized to produce 2320 kilograms steam under a pressure of 70 kilograms per square centimeter above atmospheric pressure and at a temperature of about 285°C. Of that steam, 378 kilograms are used for the partial oxidation in 1, 310 kilograms are used to preheat the oil feedstock and the oxygen, 416 kilograms are supplied to the carbon monoxide converter 7 and 1216 kilograms to the superheater of the supplementary boiler 20.

The sulfur-containing gas which has been cooled is supplied in conduit 3 to the gas desulfurization unit 4, in which the gas is scrubbed with methanol to remove COS and $H_2S$ to a residual concentration below 0.1 ppm. 2348 standard cubic meters of desulfurized gas are obtained with the following composition:

| | | |
|---|---|---|
| $CO_2$ | 5.31 | % by volume |
| CO | 47.52 | % by volume |
| $H_2$ | 46.49 | % by volume |
| $CH_4$ | 0.45 | % by volume |
| $N_2$ + Ar | 0.23 | % by volume |
| $H_2$ + COS | 0.1 | ppm |

1108 standard cubic meters of this desulfurized gas are conducted through conduits 5 and 6 to the converter 7, in which they are treated with 416 kilograms steam vapor to produce 1580 standard cubic meters of a converted gas having the following composition in percent by volume:

| | |
|---|---|
| $CO_2$ | 33.60 |
| CO | 3.50 |
| $H_2$ | 62.42 |
| $CH_4$ | 0.32 |
| $N_2$ + Ar | 0.16 |

The converted gas is conducted through conduit 8 to the scrubber 9, in which most of the $CO_2$ is removed. After the removal of $CO_2$ the gas is mixed before the fine scrubbing zone disposed at the top of the column with the unconverted partial stream from conduit 11. 2305 standard cubic meters methanol synthesis gas are conducted in conduit 10 and have the following composition in percent by volume:

| | |
|---|---|
| $CO_2$ | 3.70 |
| CO | 27.94 |
| $H_2$ | 67.67 |
| $CH_4$ | 0.46 |
| $N_2$ + Ar | 0.23 |

This gas is supplied as fresh synthesis gas into the reactor 12 and subjected therein to a methanol synthesis, by which about 1068 kilograms raw methanol and 106 standard cubic meters residual gas having a net heating value of 2740 kilocalories per standard cubic meter are produced. The raw methanol is supplied through conduit 13 to the methanol distillation unit 14, in which 1000 kilograms of pure methanol are produced.

The 612 standard cubic meters oxygen which are required for the partial oxidation are produced in the air separator 15. 390 kWh are required to compress 3060 standard cubic meters air to a pressure of 5.6 kilograms per square centimeter above atmospheric pressure and to compress the 612 standard cubic meters oxygen recovered from said air to 60 kilograms per square centimeter superatmospheric pressure. The air compressor 16 is driven by a condensing turbine 17 and the oxygen compressor 18 is driven by a back-pressure turbine 19. The air compressor 18 is driven by a back-pressure turbine 19. The air compressor 16 is driven by 1070 kilograms steam which are produced under a pressure of 33 kilograms per square centimeter above atmospheric pressure and at a temperatur of 500°C. in the methanol synthesis reactor. The oxygen compressor 18 is driven by 960 kilograms steam which are produced under a pressure of 70 kilograms per square centimeter above atmospheric pressure in the waste heat boiler 2 associated with the partial oxidation reactor and which is superheated to 500°C. in the supplementary boiler 20. 960 kilograms exhaust steam are discharged from turbine 19 under a pressure of 5 kilograms per square centimeter (absolute pressure). Of said exhaust steam, 420 kilograms are used to scrub the gas in 4 and 9 and 540 kilograms are supplied to the distillation unit 14.

The remaining 256 kilograms superheated high-pressure steam from the waste heat boiler 2 associated with the partial oxidation reactor 1 and 119 kilograms steam which have been produced and superheated in the supplementary boiler are used to drive the recycled gas compressor 21 associated with the methanol synthesis reactor by means of a back-pressure steam turbine 22. The exhaust steam in an amount of 375 kilograms and under a pressure of 5 kilograms per square centimeter (absolute pressure) is also supplied to the methanol distillation unit 14.

The steam discharged from the methanol synthesis reactor and the surplus steam discharged from the partial oxidation reactor are superheated in the supplementary boiler 20. The fuel burnt in said supplementary boiler consists of residual gases from the methanol synthesis reactor, flashed-off gas and first runnings from the methanol distillation unit, and part of the soot oil produced in the soot-processing unit.

What is claimed is:

1. In a process for producing methanol by (a) partially oxidizing a sulfur-containing high-boiling hydrocarbon in a gasification zone with oxygen and water vapor to produce a raw gas containing carbon monoxide, (b) desulfurizing the raw gas, (c) treating said desulfurized gas with water vapor to convert part of its carbon monoxide to carbon dioxide by reducing the water vapor to hydrogen thereby forming a methanol synthesis gas, and (d) producing methanol by contacting said synthesis gas with a copper-containing catalyst at elevated temperature and pressure, the improvement which comprises
   a. effecting the partial oxidation under a pressure which is at least 5 kilograms per square centimeter above the methanol synthesis pressure of step (d),
   b. effecting the desulfurization of the raw gas by washing with methanol below 0°C,
   c. treating only a portion of the desulfurized gas with water vapor to effect conversion, scrubbing that converted portion with methanol below 0°C to remove at least part of the carbon dioxide, and combining the scrubbed converted portion with the untreated portion of the desulfurized gas, and
   d. without compressing the combined gases subjecting them to the methanol synthesis at a temperature of 230° to 280°C under a pressure of 30–80 kilograms per square centimeter absolute pressure.

2. Process according to claim 1, including indirectly cooling the catalyst of step (d) with water boiling under super-atmospheric pressure thereby producing high-pressure steam, and expanding the high-pressure steam to generate power to produce compression energy for the gases to be compressed in the process.

3. Process according to claim 1 wherein the partial oxidation of the hydrocarbons is carried out under a pressure which is 10–15 kilograms per square centimeter above the pressure of the methanol synthesis.

4. Process according to claim 2 wherein the high-pressure steam produced is expanded to ambient pressure thereby generating power to produce the compression energy required to compress air from which oxygen is recovered for use in step (a).

5. Process according to claim 2 wherein the high-pressure steam produced is partly expanded to ambient pressure to provide the compression energy required to compress pure oxygen to the pressure of step (a) is also partly expanded in turbines used to recirculate synthesis gas.

6. Process according to claim 2 wherein raw methanol from step (d) is distilled, the high-pressure steam is superheated and by-products of the methanol synthesis and the subsequent distillation of methanol and part of a soot-oil mixture formed in the gas-producing plant are used as fuel for superheating.

7. Process according to claim 2 wherein low-pressure steam is produced by a partial expansion of the high-pressure steam and is supplied as a heating fluid to the unit for distilling the raw methanol product.

8. Process according to claim 1 wherein the untreated portion of the desulfurized gas of step (c) prior to combining with the treated portion is passed through a fine scrubbing zone fed with fully regenerated methanol.

9. Process according to claim 6 wherein the methanol used for scrubbing a portion of the gas in step (c) is thereafter supplied to the unit for distilling the raw methanol product.

* * * * *